Figure 1:
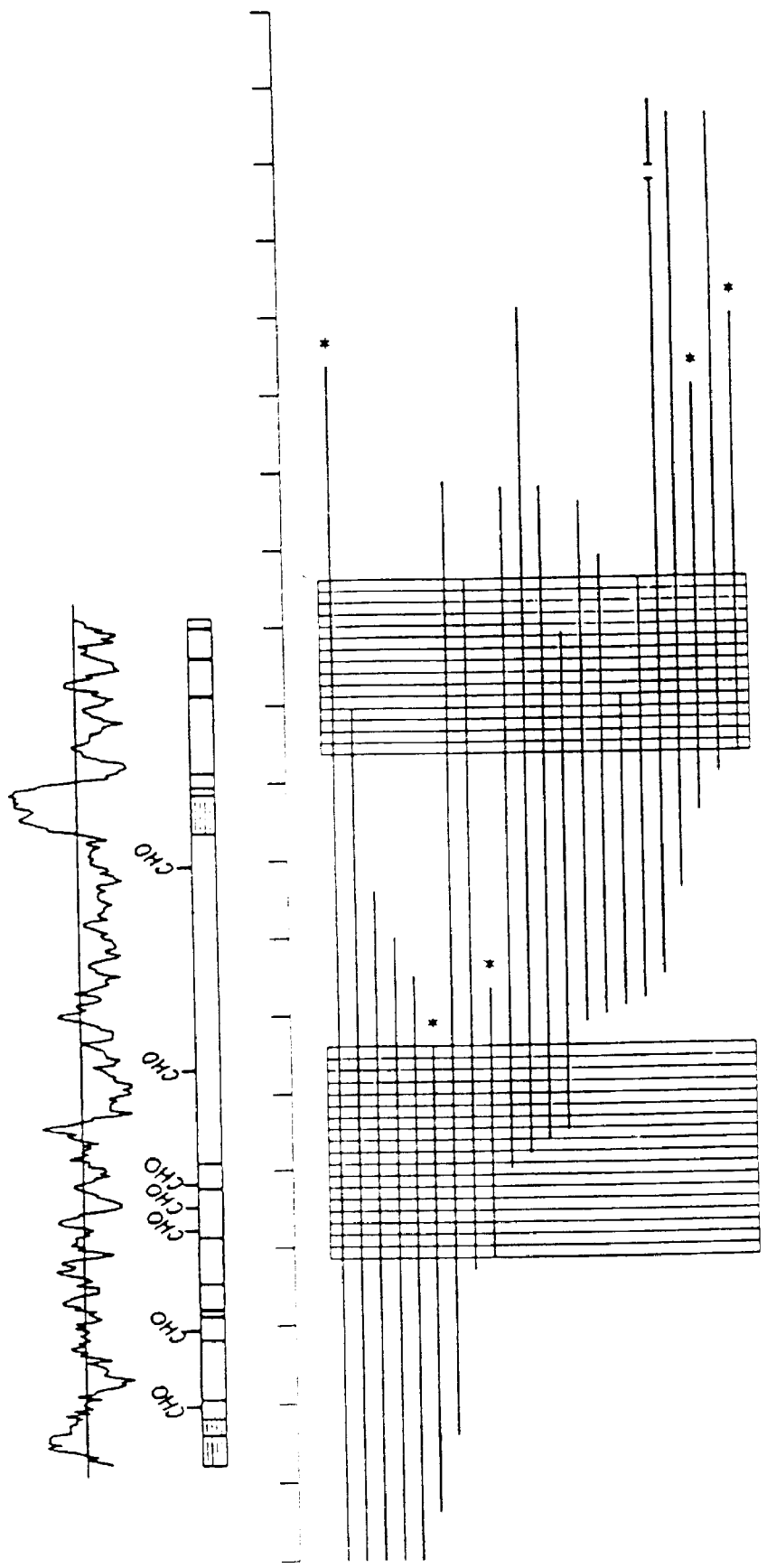

US005808004A

United States Patent [19]
St. John et al.

[11] Patent Number: 5,808,004
[45] Date of Patent: Sep. 15, 1998

[54] FRAGMENTS OF A LYMPHOCYTE ADHESION RECEPTOR FOR HIGH ENDOTHELIUM, CD44

[75] Inventors: Thomas P. St. John, Issaquah; W. Michael Gallatin, Mercer Island; Rejean L. Idzerda, Seattle, all of Wash.

[73] Assignee: Fred Hutchinson Cancer Research Center, Seattle, Wash.

[21] Appl. No.: 472,543

[22] Filed: Jun. 7, 1995

Related U.S. Application Data

[62] Division of Ser. No. 884,624, May 15, 1992, Pat. No. 5,504,194, which is a continuation of Ser. No. 628,646, Dec. 12, 1990, abandoned, which is a division of Ser. No. 325,224, Mar. 17, 1989, Pat. No. 5,002,873.

[51] Int. Cl.$^6$ .......................... C07K 14/725; C07K 14/47; C12N 15/11
[52] U.S. Cl. .......................... 530/395; 530/350; 536/23.5; 536/24.31
[58] Field of Search .................................. 530/350, 395; 536/23.5, 24.31; 935/8, 11; 436/94

[56] References Cited

U.S. PATENT DOCUMENTS

| | | | |
|---|---|---|---|
| 4,219,411 | 8/1980 | Yen et al. | 209/213 |
| 5,002,873 | 3/1991 | St. John et al. | 435/69.1 |
| 5,504,194 | 4/1996 | St. John et al. | 530/395 |

OTHER PUBLICATIONS

Aruffo and Seed, "Molecular cloning of a CD28 cDNA by a high–efficiency COS cell expression system", *Proc. Natl. Acad. Sci. USA, 84:*8573–8577 (Dec. 1987).
Barclay et al., *The Leucocyte Antigen Facts Book,* pp. 198–200, Academic Press, NY (1993).
Bevilacqua et al., "Endothelial leukocyte adhesion molecule 1: an inducible receptor for neutrophils related to complement regulatory proteins and lectins," *Science,* 243:1160–1165 (Mar. 3, 1989).
Bretcher, "Fibroblasts on the move," *J. Cell Biol., 106:*235–237 (Feb. 1988).
Bretscher et al., "Coated pits act as molecular filters," *Proc. Natl. Acad. Sci. USA, 77(7):*4156–4159 (1980).
Butcher et al., "Organ specificity of lymphocyte migration: mediation by highly selective lymphocyte interaction with organ–specific determinants on high endothelial venules," *Eur. J. Immunol., 10:*556–561 (1980).
Carter and Wayner, "Characterization of the Class III collagen receptor, a phosphorylated, transmembrane glycoprotein expressed in nucleated human cells," *J. Biol. Chem., 263(9):*4193–4201 (Mar. 25, 1988).
Dasmsky et al. Integral membrane glycoproteins in cell–cell and cell–substratum adhesion, pp. 1–64 in *The Biology of Glycoproteins,* R. J. Ivatt, Ed., Plenum Publishing Co., New York (1984).
Doege et al., Link protein cDNA sequence reveals a tandemly repeated protein structure, *Proc. Natl. Acad. Sci. USA, 83:*3761–3765 (Jun. 1986).

Edgington, "How Sweet it is: Selectin–Mediating Drugs", *Bio/Technology, 10:*383–389 (Apr. 1992).
Gallatin et al., "A cell–surface molecule involved in organ specific homing of lymphocytes," *Nature, 304:*30–34 (Jul. 7, 1983).
Gallatin et al., "Lymphocyte homing receptors", *Cell, 44:*673–680 (Mar. 14, 1986).
Griscelli et al., "The distribution of large dividing lymph node cells in syngeneic recipient rats after intravenous injection", *J. Exp. Med., 130:*1427–1451 (1969).
Guy–Grand et al., The gut–associated lymphoid system: nature and properties of the large dividing cells, *Eur. J. Immunol., 4:*435–443 (1974).
Hamann et al., "Evidence for an accessory role of LFA–1 in lymphocyte–high endothelium interaction during homing," *J. Immunol., 140(3):*693–699 (Feb. 1988).
Harris and Emery, "Therapeutic antibodies—the coming of age", *Tibtech, 11:*42–44 (Feb. 1993).
Haskard et al., "T lymphocyte adhesion to endothelial cells: mechanisms demonstrated by anti–LFA–1 monoclonal antibodies," *J. Imunol., 137(9):*2901–2906 (Nov. 1986).
Henikoff, "Unidirectional digestion with exonuclease III creates targeted breakpoints for DNA sequencing," *Gene, 28:*351–359 (1984).
Herrlich et al., "CD44 splice variants: metastases meet lymphocytes", *Immunology Today, 14(8):*395–399 (1993).
Idzerda et al., "Isolation and DNA sequence of a cDNA clone encoding a lymphocyte adhesion receptor for high endothelium," *Proc. Natl. Acad. Sci. USA, 86:*4659–4663 (Jun. 1989).
Jacobson et al., "Lateral diffusion of an 80,000–dalton glycoprotein in the plasma membrane of murine fibroblasts: relationships to cell structure and function," *J. Cell. Biol., 99:*1624–1633 (Nov. 1984).
Jalkanen et al., "A lymphoid cell surface glycoprotein involved in endothelial cell recognition and lymphocyte homing in man," *Eur. J. Immunol., 16:*1195–1202 (1986).
Jalkanen et al., "Biochemical properties of glycoproteins involved in lymphocyte recognition of high endothelial venules in man," *J. Imunol., 141(5):*1615–1623 (Sep. 1988).
Jalkanen et al., "Homing receptors and the control of lymphocyte migration", *Immunol. Rev., 91:*39–60 (1986).
Jalkanen et al., "Lymphocyte recognition of high endothelium: antibodies to distinct epitopes of an 85–95–kD glycoprotein antigen differentially inhibit lymphocyte binding to lymph node, mucosal, or synovial endothelial cells," *J. Cell Biol., 105:*983–990 (1987).
Kozak, An analysis of 5'-noncoding sequences from 699 vertebrate messenger RNAs, *Nucleic Acid Res., 15(20):*8125–8148 (1987).

(List continued on next page.)

*Primary Examiner*—Stephen Walsh
*Assistant Examiner*—Claire M. Kaufman
*Attorney, Agent, or Firm*—Marshall, O'Toole, Gerstein, Murray & Borun

[57] ABSTRACT

A lymphoid cell line cDNA that encodes an adhesion receptor for high endothelial venules (HEV).

4 Claims, 4 Drawing Sheets

OTHER PUBLICATIONS

Landau et al., "Cloning of terminal transferase cDNA by antibody screening", *Proc. Natl. Acad. Sci. USA, 81*:5836–5840 (Sep. 1984).

Lathe, "Synthetic Oligonucleotide Probes Deduced from Amino Acid Sequence Data: Theoretical and Practical Considerations", *J. Mol. Biol., 183*:1–12 (1985).

Lewinsohn et al., "Leukocyte–endothelial cell recognition: evidence of a common molecular mechanism shared by neutrophils, lymphocytes, and other leukocytes", *J. Immunol., 138*(12):4313–4321 (Jun. 15, 1987).

Liotta, "Tumor invasion and metastases–role of the extracellular matrix: Rhoads Memorial Award lecture", *Cancer Res., 46*:1–7 (Jan. 1986).

Marx, "New family of adhesion proteins discovered," *Science, 243*:1144 (Mar. 3, 1989).

Nottenburg et al., "Isolation of mouse CD44 cDNA: Structural features are distinct from the primate cDNA", *Proc. Natl. Acad. Sci. USA, 86*:8521–8525 (Nov. 1989).

Picher et al., "Monoclonal antibodies to human lymphocyte homing receptors define a novel class of adhesion molecules on diverse cell types", *J. Cell Biol., 109*(2):927–937 (Abstract Only) (Aug. 1989).

Rose et al., "Vesicular stomatitis virus glycoprotein is anchored in the viral membrane by a hydrophobic domain near the COOH terminus," *Proc. Natl. Acad. Sci. USA, 77*(7):3884–3888 (Jul. 1980).

Scollay et al., "Possible role of surface Ig in non–random recirculation of small lymphocytes", *Nature, 260*:528–529 (Apr. 8, 1976).

Seed and Aruffo, "Molecular Cloning of the CD2 Antigen, the T–Cell Erythrocyte Receptor, by a Rapid Immunoselection Procedure", *Proc. Natl. Acad. Sci. USA, 84*:3365–3369 (1987).

Siegelman et al., "Cell surface molecule associated with hlymphocyte homing is a ubiquitinated branched–chain glycoprotein," *Science, 231*:823–829 (Feb. 1986).

Siegelman et al., "Mouse lymph node homing receptor cDNA clone encodes a glycoprotein revealing tandem interaction domains," *Science, 243*:1165–1172 (Mar. 3, 1989).

Smith et al., "Migration of lymphoblasts in the rat: preferential localization of DNA–synthesizing lymphocytes in particular lymph nodes and other sites," *Monogr. Allergy,* 16:203–232 (1980).

Sofer and Britton, "Designing an Optimal Chromatographic Purification Scheme for Proteins", *Bio Techniques,* 198–203 (Nov./Dec. 1983).

St. John et al., Expression cloning of a lymphocyte homing receptor cDNA: ubiquitin is the reactive species, *Science, 231*:845–850 (Feb. 1986).

St. John et al., "Isolation and expression of a cDNA clone encoding a lymphocyte adhesion receptor for high endothelium", Abstract 1484, p. A481 of Part 1, Abstracts 1–4022, Federation of American Societies for Experimental Biology, 73rd Annual Meeting (Mar. 19–23, 1989).

Stamenkovic et al., "A Lymphocyte Molecule Implicated in Lymph Node Homing is a Member of the Cartilage Link Protein Family", *Cell, 56*:1057–1062 (Mar. 24, 1989).

Stevens et al., "Differences in the migration of B and T lymphocytes: organ–selective localization in vivo and the role of lymphocyte–endothelial cell recognition," *J. Immunol. 128*(2):844–851 (Feb. 1982).

Thiery et al., "Cell migration in the vertebrate embryo: role of cell adhesion and tissue environment in pattern formation," *Ann. Rev. Cell Biol., 1*:91–113 (1985).

von Heijne, "A new method for predicting signal sequence cleavage sites," *Nucleic Acids Res., 14*(11):4683–4690 (1986).

von Heijne, "Patterns of amino acids near signal–sequence cleavage sites," *Eur. J. Biochem., 133*:17–21 (1983).

Wayner and Carter, "Identification of Multiple Cell Adhesion Receptors for Collagen and Fibronectin in Human Fibrosarcoma cells Possessing Unique $\alpha$ and common $\beta$ subunits", *J. Cell. Biol., 105*:1873–1884 (Oct. 1987).

Weinberger et al., "Identification of human glucocorticoid receptor complementary DNA clones by epitope selection," *Science 228*:740–742 (1985).

Woodruff et al., Specific cell–adhesion mechanisms determining migration pathways of recirculating lymphocytes, *Ann. Rev. Immunol., 5*:201–222 (1987).

Yamada, "Cell surface interactions with extracellular materials," *Ann. Rev. Biochem., 52*:761–799 (1983).

Yuen et al., Applied Biosystems Protein Sequencer User Bulletin, Issue 25 (Nov. 18, 1986).

Zhou et al., "Molecular Cloning and Expression of Pgp–1 The Mouse Homolog of the Human H–CAM (Hermes) Lymphocyte Homing Receptor", *J. Immunol., 143*(10):3390–3395 (Nov. 15, 1989).

```
tcattgcccagcggacccagcctctgccaggttcggtccgccctcctcaccggccctg              60
ccccgcgccccgggatcctccagctcctctcgcctgcgccctcggttggctccggacac            120
cATGGACAAGTTTTGGTGGCGCGCAGCCTGGGGACTCTGCCTCGTGCAGCTGAGCCTGGC           180
  MetAspLysPheTrpTrpArgAlaAlaTrpGlyLeuCYSLeuValGlnLeuSerLeuAla         20
GCAGATCGATTTGAATATAACCTGTCGCTTCGAAGGTATATACCACGTGGAGAAAAATGG           240
  GlnIleAspLeuAsnIleThrCYSArgPheGluGlyIleTyrHisValGluLysAsnGly          40
TCGCTATAGCATCTCTCGGACGGAGGCAGCTGACCTCTGCAAGGCTTTCAATAGCACCTT           300
  ArgTyrSerIleSerArgThrGluAlaAlaAspLeuCYSLysAlaPheAsnSerThrLeu          60
GCCCACAATGGCCCAGATGGAGAAAGCTCTGAGCATCGGGTTTGAGACCTGCAGGTACGG           360
  ProThrMetAlaGlnMetGluLysAlaLeuSerIleGlyPheGluThrCYSArgTyrGly          80
GTTCATAGAAGGGCACGTGGTGATTCCTCGGATCCACCCCAACTCCATCTGTGCAGCAAA           420
  PheIleGluGlyHisValValIleProArgIleHisProAsnSerIleCYSAlaAlaAsn         100
CAACACAGGGGTGTACATTCTCACGTCCAACACCTCCCAGTATGACACATATTGCTTCAA           480
  AsnThrGlyValTyrIleLeuThrSerAsnThrSerGlnTyrAspThrTyrCYSPheAsn         120
TGCTTCAGCTCCACCTGGAGAAGATTGTACATCAGTCACAGACCTGCCCAATGCCTTTGA           540
  AlaSerAlaProProGlyGluAspCYSThrSerValThrAspLeuProAsnAlaPheAsp         140
TGGACCAATTACCATAACTATTGTTAACCGCGACGGCACCCGGTATGTCAAGAAAGGGGA           600
  GlyProIleThrIleThrIleValAsnArgAspGlyThrArgTyrValLysLysGlyGlu         160
ATACAGAACGAATCCTGAGGACATCAACCCCAGCAGCCCTACTGACGACGACGTAAGCAG           660
  TyrArgThrAsnProGluAspIleAsnProSerSerProThrAspAspAspValSerSer         180
CGGATCCTCCAGTGAAAGGAGCAGCACTTTAGGAGGTTACATCTTTTATAACCACTTTTC           720
  GlySerSerSerGluArgSerSerThrLeuGlyGlyTyrIlePheTyrAsnHisPheSer         200
AACTTCACCACCCATCCCAGATGAGGACGGTCCCTGGATCACCGACAGCACAGACAGAAC           780
  ThrSerProProIleProAspGluAspGlyProTrpIleThrAspSerThrAspArgThr         220
CCCTGCTACCAGAGACCAAGGTGCATTCGACCCCAGCGGGGGCTCCCATACCACTCATGG           840
  ProAlaThrArgAspGlnGlyAlaPheAspProSerGlyGlySerHisThrThrHisGly         240
ATCTGAATCAGCTGGTCATTCACATGGGAGTCGAGAAGGTGGGGCAAACACAACCTCCGG           900
  SerGluSerAlaGlyHisSerHisGlySerArgGluGlyGlyAlaAsnThrThrSerGly         260
TCCTTTAAGGACACCCCAAATTCCAGAATGGTTGATCATCTTGGCATCCCTCTTGGCCTT           960
  ProLeuArgThrProGlnIleProGluTrpLeuIleIleLeuAlaSerLeuLeuAlaLeu         280
GGCTTTGATTCTTGCAGTTTGCATTGCAGTCAACAGTCGAAGAAGGTGTGGGCAGAAGAA          1020
  AlaLeuIleLeuAlaValCYSIleAlaValAsnSerArgArgArgCYSGlyGlnLysLys         300
AAAGCTAGTGATCAACAATGGCAATGGAGCTGTGGAGGACAGAAAGTCAAGTGGACTCAA          1080
  LysLeuValIleAsnAsnGlyAsnGlyAlaValGluAspArgLysSerSerGlyLeuAsn         320
CGGAGAGGCCAGCAAGTCTCAGGAAATGGTGCATTTGGTGAACAAGGAGTCCTCAGAAAC          1140
  GlyGluAlaSerLysSerGlnGluMetValHisLeuValAsnLysGluSerSerGluThr         340
TCCAGACCAGTTTATGACAGCTGATGAGACGAGGAACCTGCAGAACGTGGACATGAAGAT          1200
  ProAspGlnPheMetThrAlaAspGluThrArgAsnLeuGlnAsnValAspMetLysIle         360
TGGGGTGtaacaccaatgccattatcttggaaagaaacaaccattggaaacataaccatt          1260
  GlyValter                                                            362
acagggagctgggacacttaacagatgcgatgtgctactgattgtttcattgggaatttt          1320
ttttttagcataaaattttctactccttattgtttttttttgtgttttgttctttaaag          1380
tcaggtccaatttttgaaaacagcattgctttctgaaattaggctccaattaataatcag          1440
caagaatttgactgttccagttcccgcatggaggcctttcatttcttggatgtgctaagg          1500
atggcttctaacacaagccacacatacatagtcccccc                                1537
```

Fig. 4.

FRAGMENTS OF A LYMPHOCYTE ADHESION RECEPTOR FOR HIGH ENDOTHELIUM, CD44

This application is a divisional of Ser. No. 07/884,624, filed May 15, 1992 (U.S. Pat. No. 5,504,194), which is a continuation of Ser. No. 07/628,646, filed Dec. 12, 1990 (now abandoned), which is a divisional of Ser. No. 07/325,224, filed Mar. 17, 1989 (U.S. Pat. No. 5,002,873).

This invention was made in part with government support under Grant CA15704 and National Cancer Institute grants CA42571 and R01 CA40272. The government has certain rights in this invention.

TECHNICAL FIELD

This invention relates to genetic engineering involving recombinant DNA technology, and particularly to the identification of a DNA sequence encoding a lymphocyte adhesion receptor for high endothelium.

BACKGROUND OF THE INVENTION

Circulating lymphocytes traffic among the blood vasculature, the lymphatic system, and sites of chronic inflammation facilitating interactions among lymphocytes, antigens, and accessory cells that ultimately lead to the generation and dissemination of an immune response. Entry of blood-borne lymphocytes into the lymphoid organs entails adhesion to the postcapillary endothelia followed by extravasation. For reviews, see: Jalkanen, S. T., et al., *Immunol. Rev.* 91: 39–60, 1986a; Woodruff, J. J., and L. M. Clarke, *Ann. Rev. Immunol.* 5: 201–222, 1987; Gallatin, M., et al., *Cell* 44: 673–680, 1986. In peripheral lymph nodes, mucosal lymphoid organs (Peyer's patches and appendix), and inflamed synovia, this adhesion-mediated entry occurs primarily at specialized high-walled endothelial cells lining the postcapillary venules (HEV). Adhesion and possibly transmigration across the venule is postulated to be mediated by a specific lymphocyte surface receptor or receptors interacting with complementary HEV molecules. These lymphocyte adhesion receptors (also referred to as homing receptors) have been implicated in the interaction of other nonlymphoid hematopoietic cells with vascular endothelia (Lewinsohn, D. M., et al., *J. Immunol.* 138: 4313–4321, 1987), and are postulated to play a role in the metastasis of lymphoid tumors (Jalkanen, S. T., et al., 1986a, supra). There is mounting evidence, discussed below, that these adhesion receptors may function widely in other tissue systems as well.

Studies conducted both in vivo and in vitro revealed that subsets of lymphocytes preferentially migrate to or adhere to the HEV of different lymphoid organs, suggesting the involvement of multiple adhesion receptors with different specificities. Griscelli, C., et al., *J. Exp. Med.* 130: 1427–1451, 1969; Guy-Grand, D., et al., *Eur. J. Immunol.* 4: 435–443, 1974; Scollay, R., et al., *Nature* 260: 528–529, 1976; Smith, M. E., et al., *Monogr. Allergy* 16: 203–232, 1980; Butcher, E. C., et al., *Eur. J. Immunol.* 10: 556–561, 1980; Stevens, S. K., et al., *J. Immunol.* 128: 844–851, 1982. Some lymphoid tumors were found to express a unispecific preference for the HEV of either peripheral lymph node or for gut-associated lymphoid tissue (Butcher, E. C., et al., 1980, supra). These data suggest the participation of at least two distinct adhesion receptors that confer lymphoid organ specificity, contributing to the migratory patterns of lymphocytes.

Direct evidence for the presence of multiple adhesion receptors emerged in rodents, humans, and nonhuman primates as immunological reagents recognizing these molecules became available. MEL-14 is a monoclonal antibody raised against a 90 kD cell-surface protein present on a peripheral node HEV-binding mouse lymphoma, 38-C13 (Gallatin, W. M., et al., *Nature* 304: 30–34, 1983). The mouse protein defined by MEL-14 is glycosylated and ubiquitinated, and contains internal disulfide bonds (Siegelman, M., et al., *Science* 231:823–829, 1986; St. John, T., et al., *Science* 231: 845–850, 1986). MEL-14 reactivity correlates with peripheral node HEV-binding specificity of B and T cell tumors; and when either normal lymphocytes or unispecific tumor cells are pretreated with the MEL-14 antibody, in vitro adhesion to peripheral node but not Peyer's patch HEV is blocked, and migration in vivo to peripheral nodes is selectively diminished (Gallatin, W. M., et al., 1983, supra).

Monoclonal antibodies (mabs) that identify glycoproteins with similar functions in primates have also been characterized: Hermes-1, which recognizes migratory competent and HEV-adherent human lymphocytes (Jalkanen, S. T., et al., *Eur. J. Immunol.* 16: 1195–1202, 1986b); Hermes-3, which specifically blocks lymphocyte binding to human appendix and Peyer's patch HEV (Jalkanen, S. T., et al., *J. Cell Biol.* 105: 983–990, 1987); and Hutch-1, which defines related molecules in macaques (W. M. Gallatin, unpublished data). All of the epitopes recognized by these mabs reside on the same molecule. Although the MEL-14 and Hermes-1 receptors are apparently immunologically related (Jalkanen, S. T., et al., 1987, supra; Jalkanen, S., et al., *J. Immunol.* 141: 1615–1623, 1988), no direct evidence indicates that they are the products of homologous genes.

Biochemical similarities between the Hermes/Hutch class of adhesion receptors and the class III extracellular matrix receptor (ECMRIII), a molecule postulated to function as a transmembrane link between the extracellular matrix and the cytoskeleton (Carter, W. G., and E. A. Wayner, *J. Biol. Chem.* 263: 4193–4201, 1988), led to a detailed comparison of the two receptors (unpublished data; T. P. St. John, W. M. Gallatin, et al.). These studies identified extensive structural homology between these molecules. The tissue distribution of ECMRIII is quite broad, including granulocytes, monocytes, fibroblasts, several epithelial carcinomas, as well as lymphocytes, indicating that these receptors may serve an adhesive function in other tissue systems.

Other classes of adhesion receptors also contribute to lymphocyte-HEV interaction. The integrin LFA-1 is important in the homotypic adhesion of activated lymphocytes and in the adhesion of T lymphocytes to endothelium (Haskard, D., et al., *J. Immunol.* 137: 2901–2906, 1986). Antibodies to LFA-1 partially inhibit lymphocyte adhesion to peripheral lymph nodes in vitro and in vivo (Hamann, D. A., et al., *J. Immunol.* 140: 693–699, 1988). However, in cell lines expressing high levels of the MEL-14 antigen, anti-LFA-1 treatment resulted in only minor reductions of HEV adhesion levels in contrast to treatment with MEL-14 antibody, which essentially eliminated adhesion to HEV. These results suggest that LFA-1 may play an accessory role in some lymphocyte-HEV interactions.

The study of HEV adhesion in the mouse has been facilitated by the exquisitely specific mab MEL-14. In the human and primate systems, the mab recognizing apparently related molecules often fail to block adhesion. The mechanism of organ specific HEV adhesion is unknown, as is the molecular basis for the functional diversity among these molecules.

SUMMARY OF THE INVENTION

We report here the molecular cloning from a baboon lymphoid cell line of a cDNA that encodes an adhesion receptor for HEV. The 362 amino acid protein encoded by this cDNA is unique and not present in all the databases examined. The mature protein, resulting from the cleavage of a putative 20 amino acid signal peptide, has a calculated molecular weight of only 37 kD, indicating that the 90 kD cell surface protein is highly modified. The 342 amino acids, which lack any repeated sequences of significant length, encompass an extracellular domain (250 amino acids), a putative transmembrane domain (20 amino acids), and a cytoplasmic domain (72 amino acids). After the cDNA sequences have been incorporated into replicable expression vectors, and the vectors transfected into an appropriate host (e.g., a mammalian, bacterial, or insect cell culture), the expressed polypeptide or polypeptides can be used to modulate mammalian immune function in at least two ways. In a first representative embodiment, the expressed product is administered in vivo in order to bind to and competitively block the lymphocyte adhesion sites on high-walled endothelial cells of postcapillary venules (HEV), and thereby prevent lymphocyte adhesion and extravasation at the complementary sites. In a second representative embodiment, the expressed product is employed as an immunogen in order to raise antibodies against lymphoid receptors for this specialized venule endothelium. The antibodies are in turn administered to directly block lymphocyte adhesion to HEV sites and thereby prevent or modulate the migration of lymphocytes from the bloodstream into the secondary lymphoid organs. Such antibodies are also useful for identifying heretofore unknown cell populations, e.g., bone marrow subsets of interest.

BRIEF DESCRIPTION OF THE FIGURES

FIG. 1 indicates the alignment of isolated cDNA clones encoding the lymphocyte adhesion receptor/ECMR III molecule, and structural features of the protein encoded by the prototype B7 cDNA clone, as described in Example 1;

FIG. 2 is an autoradiogram showing antibody binding to WGA-purified proteins from a 594S cell lysate by the crude R1594 antiserum and by antibody subsets affinity selected on the fusion protein products of the indicated individual cDNA clones, as discussed in Example 2;

FIG. 3 presents autoradiograms of the purified adhesion receptor protein (A), with (+) and without (−) subsequent cleavage by cyanogen bromide (B), as described in Example 3; and FIG. 4 shows the DNA sequence and the translated protein sequence of the prototype B7 adhesion receptor cDNA clone, as described in Example 4.

DETAILED DESCRIPTION OF THE PREFERRED EMBODIMENT

As noted above, the migration of lymphocytes from the bloodstream into the secondary lymphoid organs, necessary for a successful immune response, occurs primarily within postcapillary venules that are characterized by high-walled endothelial cells. Lymphocyte adhesion to and extravasation at these sites is associated with the expression of specific lymphoid receptors for this specialized venule endothelium. We report here the molecular cloning from a baboon lymphoid cell line of a cDNA that encodes an adhesion receptor for HEV. The cDNA clone was identified by antibody screening of cDNA-encoded fusion proteins followed by epitope selection analysis. This analysis indicated that at least two independent epitopes are detected by the antiserum probe. Amino acid sequence data on purified protein independently confirmed its identity. The 362 amino acid protein encoded by this cDNA is unique and not present in all the databases examined. The mature protein, resulting from the cleavage of a putative 20 amino acid signal peptide, has a calculated molecular weight of only 37 kD, indicating that the 90 kD cell surface protein is highly modified. The 342 amino acids, which lack any repeated sequences of significant length, encompass an extracellular domain (250 amino acids), a putative transmembrane domain (20 amino acids), and a cytoplasmic domain (72 amino acids).

It is contemplated that soluble polypeptides corresponding to the extracellular domain (amino acids 21–270) shown in FIG. 1, or antibodies directed thereto, can be administered in vivo to block, by competitive inhibition or direct interference, the entry of circulating lymphocytes into peripheral lymph nodes, mucosal lymphold organs, and/or inflamed synovia. By modulating such adhesion-mediated entry in these ways, the tissue-specific effects of the lymphocytes can be regulated for therapeutic purposes. For example, the engraftment of allogeneic tissue such as bone marrow can be enhanced in this manner. Autoimmune disease states such as rheumatoid arthritis can also be treated in this manner. Other examples include treatment of unreactive colitis, encephalitis, and other chronic site-specific inflammatory conditions.

For such purposes, the soluble external domain will often be employed, typically but not necessarily polymerized in a multivalent state using, e.g., dextran or polyamino acid carriers. Liposomes may alternatively be employed as the therapeutic vehicle, in which case the transmembrane domain (amino acids 271–290 in FIG. 1) and preferably at least some of the cytoplasmic domain (amino acids 291–362 in FIG. 1) will also be included.

For treating certain clinical conditions, it may be advisable to remove endogenous soluble receptor from a patient's blood serum, and this can be done with existing on-line and off-line techniques by employing immunoselection columns containing antibodies directed against the disclosed external domain.

The external domain can also be employed for targeting therapeutic and diagnostic moieties to HEV binding sites. For example, toxin- or radionuclide-bearing conjugates or liposomes can be directed, by incorporating the disclosed external domain moiety, to HEVs that generate at the sites of local tumor drainage, to image or disrupt the tumor blood supply.

It is understood that the particular nucleotide and amino acid sequences disclosed in FIG. 4 are representative in the sense that counterpart and related human genes and alleles can be conveniently and directly obtained pursuant to this disclosure. For example, cross-hybridization of the disclosed nucleic acid sequence(s) with genetic material from human cells, particularly lymphocytes present in chronic sites of inflammation, can be readily performed to obtain equivalent human sequences that hybridize under stringent conditions. In an analogous manner, degenerate oligonucleotides can be readily synthesized from the disclosed amino acid sequence, or portions thereof, and amplified using the polymerase chain reaction technique to obtain probes that bind to equivalent human sequences. Antibodies directed against the disclosed polypeptide can also be employed to cross-react with equivalent human and other mammalian peptides having similar epitope(s).

The following examples are presented to illustrate the advantages of the present invention and to assist one of ordinary skill in making and using the same. These examples are not intended to in any way otherwise limit the scope of the disclosure or the protection granted by Letters Patent hereon. For experimental details of Examples 1 to 5, see the appended Experimental Procedures section.

EXAMPLE 1

Immunoselection of cDNA clones with antiserum directed against ECMRIII.

RNA from a baboon lymphoid cell line, 594S, which adheres well to HEV, was used to produce a cDNA library in a bacterial expression vector, λSJ349. λSJ349 is based on λgt11 but accepts cDNA fragments in a directional fashion. cDNA fragments are inserted into the LacZ gene of the vector, resulting in the production of β-galactosidase-594S fusion proteins. Exhaustive probing of the library with monoclonal antibodies (P3H9, P1G12, Hutch-1) against the gp90 adhesion receptor was unsuccessful, indicating that these antibodies may recognize carbohydrate- or conformation-dependent epitopes. However, a rabbit polyclonal antiserum, R1594, raised to and then affinity purified with human ECMRIII, detected 12 independent antigen-expression phages of the approximately $1.5 \times 10^5$ clones that were screened. Nucleic acid hybridization data revealed that 8 of the 12 clones contained related DNA sequences; these 8 clones were further analyzed. A second screening of the library was performed using one of these clones, A10.3, as a hybridization probe. An additional 21 clones were identified. Clones identified in the initial antibody probing were code-named with an A prefix, while those obtained by hybridization were given a B prefix.

Figure 2:
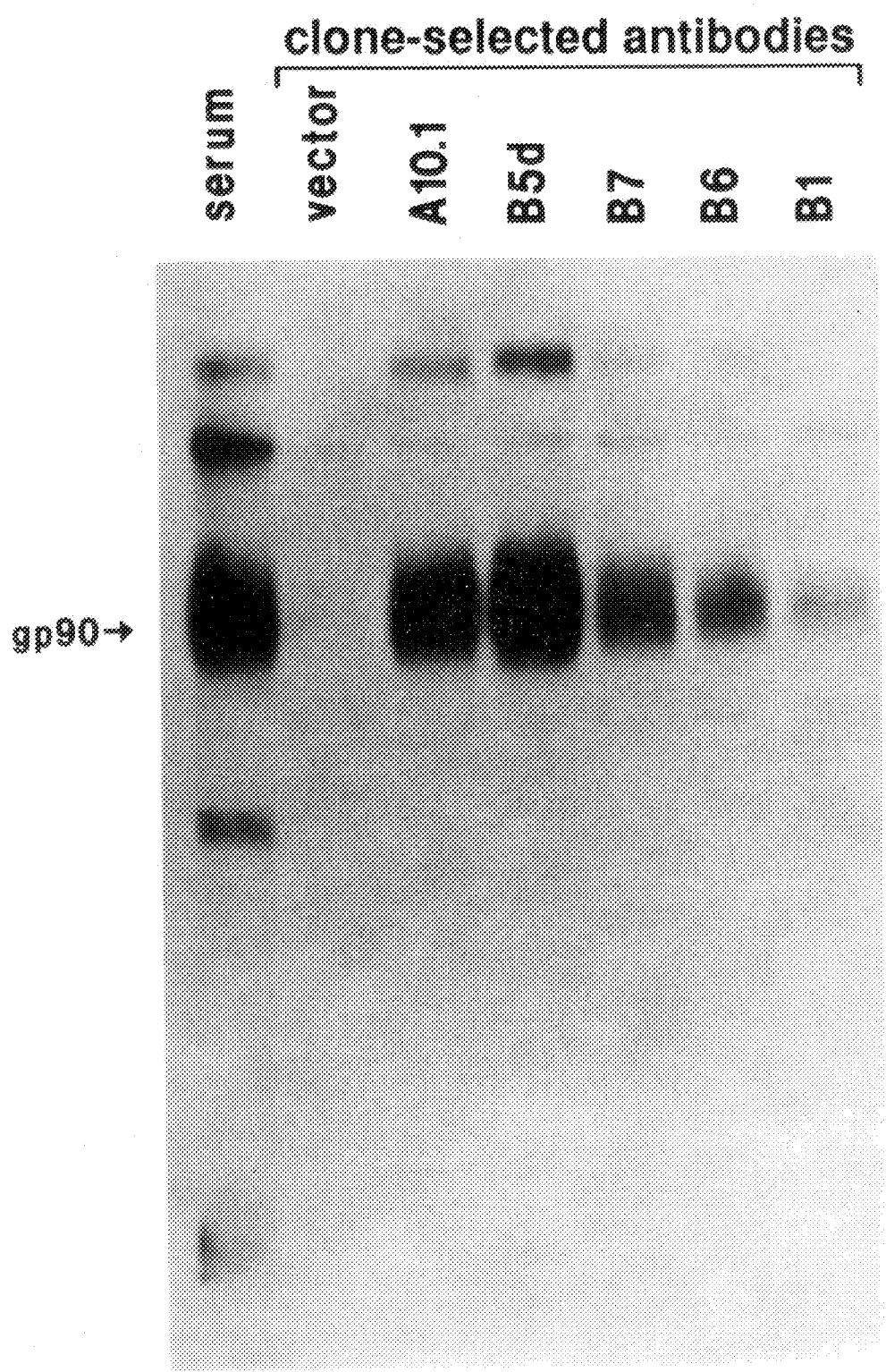

FIG. 1 is a map that indicates the alignment of 22 of the isolated cDNA clones, and structural features of the protein encoded by a prototype B7 cDNA clone. The divisions shown on the top line indicate 100 bp intervals. The prototypic clone B7 is placed at the top of the drawing, and the remaining clones are aligned to B7. The cDNA clones are, from top to bottom, B7*, B8, B44, B49, B5c, B6*, A10.3, A1.2, B1*, A11.2, B37, B56, B12, A11.1, B36, B23, B38, B34, A9.1f, A10.1*, B57, and B5d*. One clone, B34, extends approximately 1000 bp beyond the right edge of the map. All clones are derived from the λSJ349-594S cDNA library. Six clones (A series) were isolated by virtue of antibody reactivity. The original antibody reactive-oligonucleotide hybridizing clone A10.3, used as a hybridization probe in a screening of the λSJ349-594S cDNA library, allowed the isolation of 21 additional clones. 17 of these clones (B series) are shown. 12 of these 22 clones (underlined in the list below) produce R1594 antibody-reactive fusion proteins. The boxes delineate the locations of the independent 5' and 3' epitopes deduced from the location of the endpoints of the antibody-reactive clones and epitope selection analysis. Epitope selection analysis of a select 5 of these 12 (marked with an * in FIG. 1) is shown in FIG. 2.

The hydrophilic character of the polypeptide encoded by the B7 cDNA clone is shown above a block diagram of the coding region. Relative hydrophobicity is above and hydrophilicity is below the horizontal zero line. These data were calculated with a window of 7 amino acids by Genepro DNA analysis software. Potential N-linked carbohydrate sites are shown as —CHO, the locations of Cys residues as thin vertical lines, and the locations of internal Met residues as thick vertical lines. The potential signal peptide and transmembrane regions are shown hatched.

EXAMPLE 2

Multiple gp90 epitopes are encoded by the isolated cDNA clones.

The isolation of several nonoverlapping cDNA clones allowed a direct immunological demonstration that the prototype cDNA encodes the bona fide antiserum-reactive gp90 in 594S cells. This was accomplished by an epitope selection analysis (Weinberger, C., et al., Science 228: 740–742, 1985) in which nitrocellulose filters containing fusion proteins from individual clones are incubated with the polyclonal antiserum, followed by elution of the adherent antibodies. These antibodies were used to probe a transfer blot of electrophoretically separated cellular proteins. Nonoverlapping cDNA clones, bearing no common nucleic acid sequences, can present distinct epitopes and should immunoselect mutually exclusive antibody subsets from the antiserum. Epitope selection analysis was performed by incubating the R1594 antiserum with several different cDNA clones (A10.1, B5d, B7, B6, and B1) to produce clone-specific antibody subsets, which were then tested for gp90 reactivity on a Western blot containing wheat germ agglutinin (WGA)-binding proteins from 594S cells. In the resulting immunoblot, shown in FIG. 2, the first lane was probed with crude R1594 antiserum. As a negative control, epitope selection was carried out with the cloning vector containing an irrelevant insert, and the eluted antibodies were used to probe the second lane; no anti-gp90 activity was detected. The remaining lanes were probed with the antibodies selected by the indicated clones; in each case anti-gp90 activity was present.

These data can be most simply interpreted as evidence for at least two epitopes, one in the 5' and one in the 3' region of the molecule. The endpoints of the clones shown in FIG. 1 suggest map locations for these epitopes, designated by the hatched boxes. This analysis demonstrates that two (or more) distinct polypeptide epitopes expressed by the cDNA clones are shared with the 90 kD glycoprotein, providing compelling evidence for the identification of these gene sequences by serologic criteria.

Although the intensity of the bands shown in FIG. 2 suggest that the R1594 antiserum has the major portion of its activity directed against the carboxy terminal portion of the protein, the relative stabilities of the fusion proteins expressed by the clones used in the epitope selection experiment are unknown and prohibit simple interpretation of the signal strength data.

A less intense, higher molecular weight band is also present in all tracks except that of the vector, and may be a differently modified version of the same core protein as gp90. High molecular weight bands ($\geq 180$ kD) have often been seen in 594S and other cells using gp90-specific antibodies in radioimmunoprecipitation and immunoblot analyses (Jalkanen, S., et al., 1988, supra; Carter, W. G., and E. A. Wayner, 1988, supra). Our data (not shown) suggest that this higher molecular weight product shows extensive amino acid similarity with the 90 kD product, sharing at least the two regions of the protein identified above.

EXAMPLE 3

Biochemical confirmation of adhesion receptor cDNA identity.

Figures 3A, 3B:
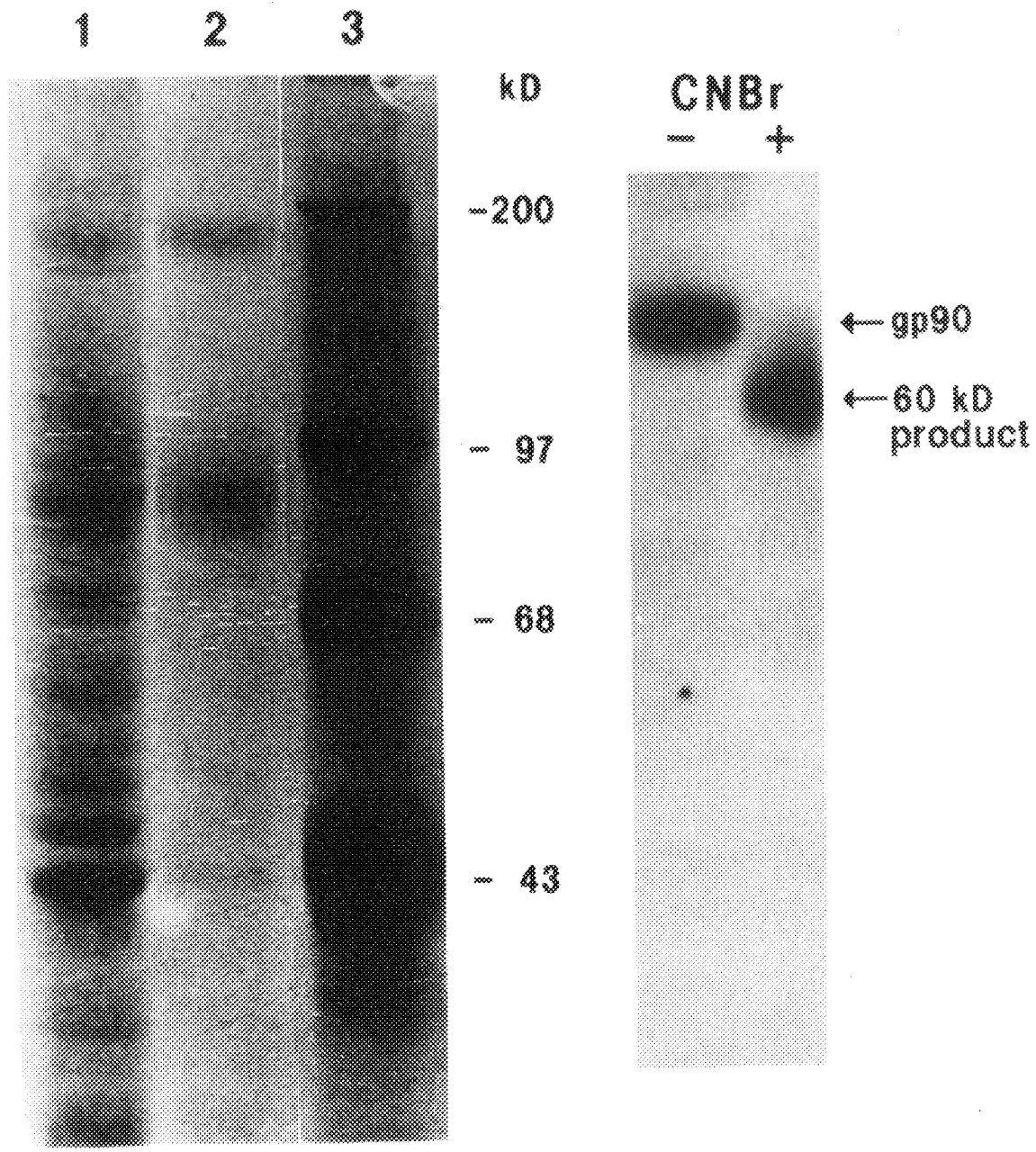

It was important to demonstrate that the isolated cDNA encodes a gp90 which is recognized by an adhesion receptor-specific monoclonal antibody and not an irrelevant gp90 which also is recognized by R1594 serum. Accordingly, Hermes-1-specific gp90 from the 594S cell line was purified and subjected to amino acid sequence analysis. The Hermes-1-specific adhesion receptor was purified from baboon 594S cells, subjected to reducing NaDodSO$_4$-PAGE (8%), and stained with Coomassie Blue R. These results are shown in FIG. 3A: partially purified protein obtained by omitting the WGA-sepharose selection step (lane 1); purified protein from $10^9$ cells (lane 2); and prestained molecular weight standards (lane 3). No sequence data was obtained on the intact protein, indicating that the N-terminus was blocked; an alternate strategy was pursued.

The effect of cyanogen bromide treatment was examined on $^{125}$I-labeled gp90 that was immunoprecipitated with Hermes-1-sepharose from a lysate of surface-labeled 594S cells. The bound proteins were eluted with propionic acid, treated with cyanogen bromide, and then electrophoresed through polyacrylamide. The autoradiogram in FIG. 3B shows the eluted material with (lane +) or without (lane −) subsequent cyanogen bromide treatment. Cyanogen bromide cleavage generates a 60 kD product. No smaller fragment(s) was apparent, presumably because it lacked $^{125}$I-labeled tyrosines.

Purified, unlabeled protein was then treated with cyanogen bromide to produce the 60 kD fragment in sufficient quantity for amino acid sequence analysis. Automated sequencing yielded the sequence Met-Val-Lys-Ala-Leu-Ser-Ile-Gly-Phe. This protein sequence information was utilized to synthesize a 256-fold degenerate 27-nucleotide oligomer whose sequence was chosen based on human codon usage tables and nearest neighbor analysis (Lathe, R., *J. Mol. Biol.* 183: 1–12, 1985). The oligomer was end-labeled with $^{32}$p and used to probe the A series cDNA clones that were identified in the initial screening of the library with R1594 antiserum. The probe hybridized under stringent conditions to the 5' end of clone A10.3 (data not shown). The nucleic acid sequence of this region of A10.3 was found to encode these amino acids of the purified protein with one exception, Glu instead of Val at position #2 (amino acids 66–74 in FIG. 4). These results confirm that this cDNA encodes this adhesion receptor for HEV. Thus the same cDNA clones were identified by independent immunological and biochemical criteria.

EXAMPLE 4

DNA sequence analysis of the adhesion receptor cDNA.

The complete DNA sequence of the B7 cDNA clone is shown in FIG. 4. The DNA sequence and the translated protein sequence of B7 cDNA clone is shown. The numbers at the right margin designate nucleotide and amino acid numbers. The putative signal peptide (AA1–20) and the putative transmembrane segment (AA271–290) indicated in FIG. 4 are shown shaded in FIG. 1. Consensus asparagine linked glycosylation sites are boxed. Cysteine residues are bold capitalized. Noncoding nucleotides are shown in lower case.

The B7 cDNA clone was chosen as the prototypic sequence based on its length and its 5' DNA sequence. The 1537 nucleotide cDNA contains one long open reading frame of 1086 bp. The 5' and 3' untranslated sequences are 121 and 330 nucleotides in length, respectively. This candidate protein coding region begins with the first Met residue encoded in any of the three reading frames. No stop codon is present upstream of the probable initiator methionine. This start location agrees well with the translation initiation consensus sequence [{GCC}GCC(A/G)CC ATGG] (Kozak, M., *Nucleic Acids Res.* 15: 8125–8148, 1987). No poly(A) tail or polyadenylation signal sequence is present, indicating that the mRNA sequence extends 3' of the cloned cDNA fragment. The DNA sequence contains no significant repeated sequences. No highly significant match to this sequence is present in the EMBL (release 17) or Genbank (release 57) databases.

EXAMPLE 5

The adhesion receptor is a transmembrane protein.

Analysis of the protein sequence deduced from the B7 cDNA DNA sequence indicates that the primary translation product consists of 362 amino acids with a predicted MW of 39.4 kD. After cleavage of the probable 20 amino acid leader peptide (see FIGS. 4 and 1), the remaining 342 amino acid protein has a predicted MW of 37.0 kD, indicating that the 90 kD cell surface form of the protein is highly modified. The proposed signal peptide cleavage site is indicated by both the (−3,−1) rule and by the weight-matrix methods (von Heijne, G., *Nucleic Acids Res.* 14: 4683–4690, 1986; von Heijne, G., *Eur. J. Biochem.* 133: 17–21, 1983).

Cyanogen bromide treatment of this gene product will generate a large fragment of 263 amino acids (66–329) corresponding to the 60 kD protein fragment whose N terminal sequence was determined above. This fragment has a calculated polypeptide MW of 28 kD, suggesting that posttranslational modification contributes approximately 32 kD of apparent MW to this region of the molecule.

A striking putative transmembrane sequence of approximately 20 amino acids (see FIGS. 4 and 1) begins after a mature external domain of 250 amino acids. The cytoplasmic domain of 72 amino acids is highly charged (32% charged residues). The relatively hydrophilic external domain contains only 10% charged amino acids. The C terminal 50% of the external domain is significantly more hydrophilic than the N terminal 50% (FIGS. 1 and 4.

The mature protein contains 7 potential sites of attachment of asparagine linked carbohydrate distributed along the mature external domain of the protein in general agreement with the number (8–10) of N linked sugars determined for the human product (Carter, W. G., and E. A. Wayner, 1988, supra).

The mature protein contains 8 Cys residues (FIG. 1, thin lines; and FIG. 4, caps). One of these residues is located in the putative transmembrane segment while another is positioned just inside the cytoplasmic domain near the membrane where it may be available for membrane attachment via a thioester bond to a fatty acid. This residue, $Cys_{296}$, is flanked on the N terminal and C terminal sides by 3 Arg and 3 Lys residues, respectively. These charged residues may interact with the negatively charged phospholipids on the cytoplasmic side of the membrane bilayer. Similar sequences are found in VSV G protein whose Cys residue is acylated with palmitic acid (Rose, J. K., et al., *Proc. Natl. Acad. Sci. USA* 77: 3884–3888, 1980).

The remaining 6 Cys residues are spaced throughout the N terminal 44% of the external domain. At least one pair of these residues probably forms a disulfide bond, as indicated by the decrease in mobility during electrophoresis under reducing conditions (Jalkanen, S. T., et al., 1986b, supra). These observations, the presence of multiple Cys residues, and the electrophoretic mobility behavior suggest that the N terminal half of the external domain of the molecule may be a relative compact, folded structure.

The protein lacks an RGD sequence, consistent with our experiments indicating that lymphocyte adhesion to high endothelium does not involve the RGD recognition sequence (data not shown). The protein sequence of this glycoprotein is unique in the Protein Identification Resource (PIR, release 16) database and both the EMBL and Genbank DNA databases translated into all 6 reading frames. An intriguing sequence similarity in the PIR database was found with mouse link protein, a hyaluronic acid binding protein present as a structural component of proteoglycans (Doege, K., et al., *Proc. Natl. Acad. Sci. USA* 83: 3761–3765, 1986). This similarity (a match of 28/101 residues, or a match of 41/101 including conservative amino acid changes, and 20% exact matches overall) includes 4 of the Cys residues of the external domain.

The isolation of the gene sequences encoding the lymphocyte adhesion receptor/ECMRIII molecule now provides the means for a direct determination of the structure and function of this abundant cell surface molecule. Two functions have been determined for this molecule: the adhesion to mucosal HEV which is directly interfered with by mab to this molecule, and the adhesion of this molecule to Types I and VI collagen. The structure and role of posttranslational modifications in the function of this molecule will be facilitated by the manipulation of the amino acid sequence. Using molecular genetic methods, one can directly determine which areas of the molecule participate in adhesion to HEV and to collagen.

The receptor molecule is heavily modified, with the 37 kD core polypeptide holding 53 kD of apparent MW of posttranslational modification. These modifications include both N- and O-linked glycosylation, addition of the glycosaminoglycan chondroitin sulfate yielding a multitude of larger antigens, addition of sulfate, and the addition of phosphate to cytoplasmic domain serine residues (Jalkanen, S., et al., 1988, supra; Carter, W. G., and E. A. Wayner, 1988, supra). Other potential modifications may include ubiquitin and a fatty acid addition. The mouse mab MEL-14 has been shown to recognize the polypeptide ubiquitin (Siegelman, M., et al., 1986, supra; St. John, T., et al., 1986, supra). Jalkanen et al. (1987 and 1988, supra) has shown that this mab also recognizes the human pg90 and gp180–200 products, and that preclearance with the Hermes-1 antibody removes all MEL-14 reactive material. These data suggest that ubiquitin epitope(s) may also reside on the primate molecule, although no evidence for a ubiquitin N-terminus was found in the protein sequence data derived from either the N-terminus or the largest CNBr fragment. The deduced protein sequence suggests that the Cys residue located in the cytoplasmic domain near the inner membrane surface may be a point of attachment for a fatty acid. However, the addition of such a molecule would have little effect on the apparent MW of the mature protein.

Although differences in the quantity or quality of these modifications may play a direct role in the determination of the organ specificity of HEV adhesion, variously modified molecules have not been correlated with the organ specific HEV adhesion phenotype (Jalkanen, M., et al., 1988, supra). Small but important differences may have been overlooked due to the diffuseness of the 90 kD band. The possibility exists that the more easily examined 90 kD molecule is not the actual adhesion structure. Rather, adhesion to mucosal HEV may be facilitated by one of the larger MW forms of the molecule. Modifications of the 180–200 kD forms would go undetected due to the minute effect these alterations would likely have in such a large structure.

In vivo, lymphocyte transmigration from the blood vasculature into the parenchyma of a lymph node is preceded by adhesion to specialized high endothelial cells lining the venules within the node. By definition, the adhesion receptors function in this first stage of adhesion, but how they contribute to the subsequent extravasation process and whether additional lymphocyte surface structures are required for the latter process is unknown. In general, cell adhesion and mobility are processes that involve the cytoskeleton and require interaction with the extracellular matrix (Bretscher, M. S., *J. Cell. Biol.* 106: 235–237, 1988; Damsky, C. H., et al., in The Biology of Glycoproteins, R. J. Ivatt, ed., Plenum Publishing Co., New York, N.Y., p. 1, 1984; Yamada, K. M., *Ann. Rev. Biochem.* 52: 761–799, 1983). The recent finding that the ECMRIII/HEV adhesion receptors, major cell surface proteoglycans, bind the extracellular matrix component, collagen, and are associated with the cytoskeleton (Carter, W. G., and E. A. Wayner, 1988, supra) suggests the possibility that they provide a transmembrane link that may facilitate adhesion and perhaps even participate in transmigration into the lymph node. This type of cytoskeletal attachment manifests itself in the rather low diffusion constant (Jacobson, K., et al., *J. Cell. Biol.* 99: 1624–1633, 1984) exhibited by the cell surface molecule and results in its exclusion from coated pits (Bretscher, M. S., et al., *Proc. Natl. Acad. Sci. USA* 77: 4156–4159, 1980). The approximately 70 cytoplasmic domain amino acids of the gp90 receptor may be involved in the attachment of this protein to the cytoskeleton.

How does one account for the observations that the proteins independently identified as the collagen-binding ECMRIII and the adhesion receptor for HEV are nearly ubiquitous in tissue distribution yet mediate lymphoid organ-specific adhesion of lymphocytes? And what function do these receptors have in other tissue systems? Multiple organ specific adhesion specificities may result from the expression of independent receptor molecules whose diversity is controlled by gene sequence, gene structure, or from variations in posttranslational additions of carbohydrate, ubiquitin, phosphate other moieties, or by a combination of these mechanisms. Equally simple, these organ specificities may be dictated by the sum of the specificities of several independent receptor systems (including non-gp90 types). Any of these mechanisms might be sufficiently cell-type-specific and temporally regulated to result in the expression of different adhesion specificities in different cell types or stages of cell maturation. In nonlymphoid cells, the adhesion receptors may be important in cell mobility, tumor metastasis, and embryonic development, phenomena that involve cell adhesion to extracellular matrix proteins (Bretscher, M. S., 1988, supra; Damsky, C. H., et al., 1984, supra; Bretscher, M. S., et al., 1980, supra; Liotta, L. A., *Cancer Res.* 46: 1–7, 1986; Thiery, J. P., et al., *Ann. Rev. Cell. Biol.* 1: 91–113, 1985). Further biochemical characterization of both the lymphocyte and endothelial components involved in recirculation will clarify the molecular basis of their interaction and their roles in adhesion and extravasation.

Experimental Procedures cDNA Library Construction. Poly(A) containing RNA from a baboon lymphoid cell line, 594S (Rabin, H., et al., *Intervirology* 8: 240–249, 1977), was reverse transcribed and homopolymer tails added to the 3' end of the cDNA product by terminal deoxynucleotidyltransferase in the presence of dGTP. A 25 base oligonucleotide, 5'GGG GCGGCCGCCCCCCCCCCCCCCC 3', was annealed to the tailed cDNA and extended with *E. coli* DNA polymerase I. This material was ligated with EcoRI adaptors, cleared with NotI, and material larger than≈350 bp purified by gel electrophoresis. This cDNA synthesis procedure produces cDNA fragments flanked by NotI and EcoRI sites at the 5' and 3' termini, respectively. cDNA was ligated with the purified left and right arms of λSJ349 DNA that had been cleaved with EcoRI and NotI, in vitro packaged, and amplified by growth on the bacterial strain Y1090.

λSJ349. The λSJ349 vector is a directional cloning version of λgt11 produced by the insertion of a 33 bp oligonucleotide (AATTGGGCCCAATGCATTGGCGCCGCGGCCGCG) at the λgt11 EcoRI site. The orientation of insertion of this oligo as an EcoRI fragment results in a single NotI site upstream of the single EcoRI site. A 1304 base pair stuffer fragment containing the E. coli rpsL gene allows the EcoRI-NotI digestions to proceed more efficiently.

Preparation of Rabbit Polyclonal Anti-gp90 Antibodies (R1594). The 90 kD antigen was purified from HT1080 human fibrosarcoma cells as previously described (Carter, W. G., and E. A. Wayner, *J. Biol. Chem.* 263: 4193–4201, 1988) followed by preparative SDS-PAGE. A New Zealand white rabbit was immunized with this material. The resulting antiserum was affinity purified on immobilized gp90 (purified with the P3H9 mab).

Antibody Screening of Phage Library. The resulting library was plated and the released β-alactosidase fusion proteins transferred to nitrocellulose filters. These filters were incubated with the R1594 rabbit serum followed by $^{125}$I-protein A as described previously (Landau, N. R., et al., *Proc. Natl. Acad. Sci. USA* 81: 5836–5840, 1984). Positive clones were purified by dilution and reprobing.

Epitope Selection and Protein Blotting. Five antiserum-reactive recombinant clones and the λSJ349 vector (containing an irrelevant insert) were used for epitope selection essentially as previously described (Weinberger, C., et al., 1985, supra). Clones were plated, transferred to nitrocellulose filters, and then incubated with crude R1594 antiserum (diluted 1:100). Filters were washed, and the bound antibodies were eluted in 50 mM glycine, pH 2.5/0.1% NP40/0.15M NaCl, neutralized with 2M Tris, pH 8.0, and used to probe a protein gel blot. WGA-selected 594S cell proteins (prepared as described below) were subjected to reducing NaDodSO$_4$-PAGE, and transferred to a nitrocellulose filter. The filter was cut into strips which were probed with the crude serum or clone-selected antibodies, as indicated. The strips were then incubated with $^{125}$i-labeled protein A (0.5×10$^6$ cpm/ml). After washing, the strips were subjected to autoradiography.

Protein Purification and Chemical Cleavage. 594S cells were grown to a density of 2×10$^6$ cells/ml in RPMI1640/10% fetal calf serum and lysed in 3% NP40/20 mM Tris, pH 7.4/0.15M NaCl. The lysate was centrifuged at 27k rpm in an SW50.1 for 30 minutes at 4° C., and the cleared supernatant was batch-loaded onto WGA-sepharose. Bound proteins were eluted in 0.2M N-acetylglucosamine in the lysis buffer, and batch-loaded onto sepharose conjugated with Hermes-1. Proteins were eluted from the immunoaffinity column in 50 mM glycine, pH 2.5/0.3% NP40/0.15M NaCl, then dialyzed and precipitated with ethanol.

$^{125}$I-labeled adhesion receptor was immunoprecipitated with Hermes-1-sepharose from a lysate of 594S cells that had been surface-iodinated using lactoperoxidase catalysis. Bound labeled proteins were eluted in 1M propionic acid, then half of the sample was exposed to cyanogen bromide at ambient temperature overnight. Samples were lyophilized in a speed-vac, then electrophoresed through a 12% polyacrylamide gel under reducing conditions and autoradiographed.

Protein Sequence Determination. NaDodSO$_4$-PAGE was performed under conditions appropriate for amino acid sequence analysis, proteins were transferred to derivatized GF/F paper, stained, and the gp90 band was excised for automated sequencing as previously described (Applied Biosystems Protein Sequencer User Bulletin, Issue 25, Nov. 18, 1986).

Oligonucleotide Hybridization. The 27 bp oligonucleotide was end labeled with $^{32}$p by T$_4$ polynucleotide kinase. Hybridization was conducted with 2.5×10$^6$ cpm/ml at 52° C. in 5× SSPE/0.1% Ficoll/0.1% bovine serum albumen/0.196 *polyvinyl pyrrolidone, followed by repeated washing at room temperature in* 5× SSPE. 1× SSPE is 0.18M NaCl/10mM Na$_{1.5}$PO$_4$/2mM Na$_2$EDTA, pH 7.0.

DNA Sequence Determination. Sequence was determined of both DNA strands by a combination of ExoIII deletion methods (Henikoff, S., *Gene* 28: 351–359, 1984) and through the use of specific synthetic oligonucleotides located approximately 200 bp apart along the cDNA sequence. Sequencing reactions were performed with Sequenase™ kit reagents (United States Biochemical Corp.) according to the manufacturer's recommendations.

Oligonucleotide Primer Extension. An mRNA complementary oligonucleotide (nuc. 179–208) was synthesized, phosphorylated with λ$^{32}$-P-ATP (3000 Ci/mmol), annealed to 594S mRNA and extended with reverse transcriptase. 380,000 cmp of oligonucleotide and 2 μg of RNA were used. Extensions were performed with the human cell line Daudi mRNA and the mouse T lymphoma EL4 mRNA as controls. The length of the visible bands was determined by the electrophoresis of DNA sequencing reactions in adjacent tracks.

EXAMPLE 6

Cell surface expression of the primate adhesion receptor on mouse L cells.

To determine whether B7 encodes an expressible cell surface protein reactive with the available battery of adhesion receptor-specific antibodies, the B7 cDNA insert was subcloned into a mammalian expression vector carrying the SV40 early gene region enhancer and promoter, donor and acceptor splice sites, and a polyadenylation signal. Using a calcium-phosphate precipitation technique, this B7 containing plasmid was cotransfected with a plasmid containing the neomycin resistance gene into mouse L cells. Sixteen independent stable transfectants expressing the neomycin resistance gene were selected by growth in medium containing G418. Of these, ten expressed the adhesion receptor on the cell surface as visualized by fluorescence microscopy after staining with the anti-ECMRIII monoclonal antibodies, P1G12 and P3H9, as well as the adhesion receptor-specific Hermes-1 monoclonal antibody. Flow cytometry analysis was performed on a representative L cell transfectant, LB7-6, as well as on nontransfected L cells and the baboon lymphoid 594S cell line. The data demonstrated unimodal staining of the lymphoid cells and the L cell transfectants with each monoclonal antibody, while the nontransfected cells were negative. That p3H9, P1G12, and Hermes-1 all stained the transfectants confirms that each recognizes the same B7-encoded surface protein that is expressed in 594S cells. Whether additional gp90 adhesion receptor species are present on the 594S cell surface is unknown. It is very unlikely that the transfection procedure itself activates a previously silent mouse gene or alters a normal mouse protein resulting in a detectable product, because not all neomycin-resistant L cell transfectants expressed the adhesion receptor. Nor did cells transfected with the neomycin resistance gene alone stain the adhesion receptor-specific antibodies.

The recognition of the clone B7-encoded protein in L cell transfectants by the anti-ECMRIII monoclonal antibodies, P1G12 and P3H9, as well as by the anti-adhesion receptor antibody, Hermes-1, provides genetic confirmation that these antibodies recognize the same protein. Many of the characteristic traits of the ECMRIII/adhesion receptors, including acidic isoelectric point, size, glycosylation, phosphorylation, and widespread tissue-distribution, are also exhibited by several other 80–95 kD membrane proteins. These include: CD44, and 80 kD protein associated with thymocyte maturity, also referred to as p80-A1G3; Pgp-1 and related molecules; and a gp85 that is linked to the cytoskeleton via attachment to ankyrin. It has been suggested that CD44 and the ankyrin-binding gp85 are identical to or at least antigenically related to Pgp-1. The possibility that these 80–95 kD proteins may be related to the adhesion receptor for HEV has been raised. To investigate the relationship between these molecules and the clone B7-encoded adhesion receptor, we examined LBU-6 transfectants, non-transfected L cells, and 594S cells for CD44 expression with the anti-CD44 monoclonal antibody, A1G3. The resulting flow cytometry analysis showed that A1G3 stains 594S cells, the transfectant LB7 cell line, but not nontransfected L cells. Thus, the adhesion receptor encoded by clone B7 is a CD44 molecule. It has been reported that CD44 is distributed throughout the body, but in the thymus is restricted to medullary thymocytes where it is acquired during T cell maturation. These findings are consistent with the known distribution of adhesion receptors.

Biochemical information about the expression of the primate adhesion receptor in mouse L cell transfectants was obtained by radioimmunoprecipitation analysis on the three most brightly staining transformants, LB7-2, LB7-6, and LB7-7, in parallel with 594S cells and nontransfected L cells. Cells were surface iodinated with $^{125}$I, solubilized in NP-40 and the lysate was incubated with the P3H9 antibody and Protein A-sepharose. The bound proteins were subjected to reducing SDS-PAGE and autoradiographed. As before, the 594S protein migrated as a diffuse band around 92 kD. Each of the L cell transfectants produced a P3H9-specific surface protein of 88 kD, indicating a high degree of posttranslational modification. Differences in glycosylation or other modifications might account for the small discrepancy observed in protein size between the mouse transfectants and the baboon 594S cells.

Expression of the primate adhesion receptor for HEV on the surface of mouse L cells provided the opportunity to determine whether it conferred a new behavior on L cells, the ability to adhere to primate HEV. Adhesion to peripheral lymph node HEV was examined in vitro with B7-transfected L cell lines, nontransfected L cells, and baboon lymphoid 594S cells. The test cells, along with directly fluoresceinated 594S cells (as an internal control) were incubated on frozen sections of primate peripheral lymph node, washed, fixed, and the adherent cells counted. The number of adherent test cells was normalized to the number of adherent internal control cells, providing an adhesion ratio. The adhesion ratio of the LB7-6 transfectants was 1.5-fold greater than that of nontransfected L cells, while 594S cells adhered 3.5-fold better. However, the nontransfected L cells themselves exhibited a higher level of adhesion to the lymph node HEV than is typically observed with nonbinding lymphoid tumors. Perhaps mouse L cells (fibroblasts) express other adhesion molecules that mediate a basal level of adhesion to HEV, such as a member of the integrin family of adhesion receptors. That mouse L cell transfectants do not exhibit a level of adhesion comparable to 594S cells might result from a variety of factors, such as species differences in the structure and function of accessory molecules, the lack of necessary accessory molecules, and gross morphological differences in L cell fibroblasts compared with lymphocytes. We are currently investigating whether expression of clone B7 in a hematopoietic cell background will confer a level of adhesion comparable to peripheral node-binding lymphoid cells.

EXAMPLE 7

As discussed above, we have identified extensive structural homology between one type of heterotypic adhesion receptor (HAR) involved in lymphocyte interactions with high endothellum in lymphold organs and a collagen-binding protein, termed extracellular matrix receptor III (ECMRIII) expressed on most nucleated cell types. Both receptors have been described as heterogeneous 90 kDa transmembrane glycoproteins, referred to here as GP90. In the additional experiments summarized below, monoclonal anti-HAR antibodies, Hermes-1 and Hutch-1, and monoclonal anti-ECMRIII antibodies, P1G12 and P3H9, were utilized to compare the two receptors. The following observations were made: (i) All these monoclonal antibodies (mabs) immunoprecipitated major GP90 components as well as uncharacterized additional higher molecular mass antigens of 120–200 kDa in human and macaque fibroblast and peripheral blood mononuclear cells (PBMC). (ii) Competitive binding analyses with the antibodies identified distinct epitopes present on GP90. (iii) Enzymatic and chemical digestions generated identical peptide fragments from all the antigens in human and macaque fibroblasts and PBMC. (iv) Sequential immunoprecipitation with P1G12 followed by the other mabs indicated that all GP90 species reactive with Hermes-1 and Hutch-1 also expressed the P1G12 defined epitope. In reciprocal experiments, Hermes-1 and Hutch-1 immunoprecipitation did not completely remove all P1G12-reactive GP90 from cellular extracts. One inference from these data would be that GP90 is serologically heterogeneous encompassing HARS as a major subset of this broadly expressed class of molecules.

While the present invention has been described in conjunction with a preferred embodiment, one or ordinary skill, after reading the foregoing specification, will be able to effect various changes, substitutions of equivalents, and other alterations to the compositions and methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. An isolated polypeptide comprising a fragment of a lymphocyte adhesion receptor selected from the group consisting of:
   (a) amino acid residues 21 through 270 of the sequence set forth in FIG. 4,
   (b) amino acid residues 271 through 290 of the sequence set forth in FIG. 4,
   (c) amino acid residues 21 through 290 of the sequence set forth in FIG. 4,
   (d) amino acid residues 271 through 362 of the sequence set forth in FIG. 4, and
   (e) amino acid residues 291 through 362 of the sequence set forth in FIG. 4, said polypeptide being free of proteins from the same mammal.

2. An isolated polynucleotide sequence encoding the polypeptide of claim 1.

3. The polynucleotide sequence of claim 2 which is a DNA.

4. The DNA of claim 3 selected from the group consisting of:
   (a) nucleotides 182 through 931 of the sequence set forth in FIG. 4,
   (b) nucleotides 932 through 991 of the sequence set forth in FIG. 4,
   (c) nucleotides 182 through 991 of the sequence set forth in FIG. 4,
   (d) nucleotides 932 through 1207 of the sequence set forth in FIG. 4, and
   (e) nucleotides 992 through 1207 of the sequence set forth in FIG. 4.

* * * * *